United States Patent
Putz

(10) Patent No.: US 9,072,864 B2
(45) Date of Patent: Jul. 7, 2015

(54) CATHETER WITH DEPTH ELECTRODE FOR DUAL-PURPOSE USE

(71) Applicant: Ad-Tech Medical Instrument Corporation, Racine, WI (US)

(72) Inventor: David A. Putz, Pewaukee, WI (US)

(73) Assignee: Ad-Tech Medical Instrument Corporation, Racine, WI (US)

( * ) Notice: Subject to any disclaimer, the term of this patent is extended or adjusted under 35 U.S.C. 154(b) by 419 days.

(21) Appl. No.: 13/687,254

(22) Filed: Nov. 28, 2012

(65) Prior Publication Data

US 2014/0148780 A1 May 29, 2014

(51) Int. Cl.

| A61M 5/00 | (2006.01) |
|---|---|
| A61M 25/00 | (2006.01) |
| A61B 5/00 | (2006.01) |
| A61B 5/0478 | (2006.01) |
| A61N 1/05 | (2006.01) |
| A61N 1/36 | (2006.01) |
| A61M 25/01 | (2006.01) |
| A61B 5/06 | (2006.01) |

(52) U.S. Cl.
CPC ......... *A61M 25/0052* (2013.01); *A61M 25/007* (2013.01); *A61M 2025/0063* (2013.01); *A61M 2025/0166* (2013.01); *A61M 2210/0693* (2013.01); *A61B 5/6852* (2013.01); *A61B 5/6868* (2013.01); *A61B 5/0478* (2013.01); *A61B 5/065* (2013.01); *A61B 5/4836* (2013.01); *A61N 1/0534* (2013.01); *A61N 1/36025* (2013.01); *A61N 1/36064* (2013.01)

(58) Field of Classification Search
CPC .... A61B 5/0478; A61B 5/065; A61B 5/6868; A61M 2025/0166; A61M 2210/0693; A61N 1/0534; A61N 1/36025; A61N 1/36064
USPC .......................................................... 604/117
See application file for complete search history.

(56) References Cited

U.S. PATENT DOCUMENTS

| 4,386,615 A | 6/1983 | Sowton |
| 4,540,402 A | 9/1985 | Aigner |
| 4,723,556 A | 2/1988 | Sussman |
| 5,119,832 A | 6/1992 | Xavier |
| 5,423,882 A | 6/1995 | Jackman et al. |
| 5,531,673 A | 7/1996 | Helenowski |
| 5,785,706 A | 7/1998 | Bednarek |
| 5,868,706 A * | 2/1999 | Cox ........................... 604/96.01 |
| 6,210,346 B1 | 4/2001 | Hall et al. |
| 7,150,737 B2 | 12/2006 | Purdy et al. |
| 7,322,954 B2 * | 1/2008 | Putz ................................ 604/43 |
| 2007/0161919 A1 | 7/2007 | DiLorenzo |
| 2009/0264817 A1 | 10/2009 | Flach et al. |
| 2011/0190712 A1 * | 8/2011 | Ciavarella et al. ............ 604/265 |

* cited by examiner

*Primary Examiner* — Kevin C Sirmons
*Assistant Examiner* — Deanna K Hall
(74) *Attorney, Agent, or Firm* — Jansson Munger McKinley and Shape Ltd.

(57) ABSTRACT

A catheter assembly for intracranial treatment of a patient for facilitating concurrent electrical sensing and fluid flow is provided and includes an outer flexible tube having a proximal end, a principal lumen extending therealong to the proximal end, and at least one radial aperture through the wall communicating with the lumen as well as a secondary lumen adjacent to the tube outer-wall surface and extending therealong. The catheter assembly including a depth electrode within the secondary lumen, extending along the length thereof. The depth electrode having electrical contacts exposed to brain tissue along the flexible tube.

27 Claims, 8 Drawing Sheets

CATHETER WITH DEPTH ELECTRODE FOR DUAL-PURPOSE USE

FIELD

The present invention relates to catheter assemblies for treatment of brain tissue and to devices for electrical stimulating/monitoring of brain activity.

BACKGROUND

Depth electrodes have been utilized for a variety of brain-monitoring and brain-stimulating purposes related to epilepsy and a variety of movement disorders. For example, monitoring of electrical activity is important in ascertaining the focus of epileptogenic brain tissue and cells for the purpose of determining possibilities for later removal or treatment. Furthermore, highly-targeted electrical stimulation using depth electrodes has been used to suppress undesirable behavior resulting from various movement disorders.

Small brain-insertable catheters have been used for a variety of fluid-removal and drug-delivery purposes. Fluid removal is often necessary or helpful in connection with brain injuries; likewise highly-targeted drug delivery to very specific portions of brain tissue is useful in a variety of medical situations.

In a number of specific situations, insertion of both catheter devices and depth electrode devices is medically appropriate or helpful, but this of necessity has involved plural insertions into brain tissue. Fluid-movement and electrical functions are often needed or highly desirable at essentially the same locations within the brain tissue. It should be evident that insertions into brain tissue are risky procedures and that minimizing the number of insertions is desirable.

A wide variety of probes have been created and are available. However, there is a need for improvement in brain-insertable probes, and it is to this need that this invention is directed.

SUMMARY

In accordance with the present device, an intracranial catheter assembly is provided for precise treatment of brain tissue. The catheter assembly of this invention overcomes certain problems and shortcomings of the prior art and provides a unique structure satisfying plural intracranial monitoring and treatment needs.

The catheter assembly of this invention includes (a) an outer flexible tube having a proximal end, a principal lumen extending therealong to the proximal end, and at least one radial aperture through the wall communicating with the lumen, the tube further defining a secondary lumen adjacent to the tube outer-wall surface and extending therealong to the proximal end, and (b) a depth electrode within the secondary lumen, extending along the length thereof and out the proximal end, the depth electrode having spaced electrical contacts exposed along the flexible tube, thereby facilitating concurrent electrical sensing and fluid flow.

In highly preferred embodiments, the outer tube includes windows therethrough which are aligned with the electrical contacts of the depth electrode. It is also highly preferred that the catheter assembly include a plurality of radial apertures axially-spaced along and around the outer tube. In certain preferred embodiments the outer tube has a closed distal end.

In preferred embodiments, the assembly further includes a rigid stylet received within the principal lumen for purposes of insertion of the catheter assembly into the patient's brain. The rigid stylet is withdrawn from the assembly after insertion is complete.

In some embodiments, a luer fitting is inserted into the principal lumen at the proximal end during treatment. In such embodiments, the luer fitting is a connector for connecting the catheter assembly with a drainage system or other device.

In certain embodiments, the electrical contacts along the depth electrode have diameters such that they extend at least partially into the windows, thereby facilitating their electrical contact with brain tissue. In other embodiments, the electrical contacts along the depth electrode are substantially flush with the outer-wall surface.

In some embodiments, in cross-section the principal and secondary lumens of the catheter assembly are substantially circular, the size of the secondary lumen is smaller than the size of the principal lumen, and the tube outer-wall surface is substantially smooth and has a major portion (cylindrical) substantially parallel to the surface of the principal lumen, a minor portion (cylindrical) substantially parallel to the surface of the secondary lumen, and transitional portions therebetween on either side. Such transitional portions are other than concave; it is preferable that in cross-section each transitional portions be substantially linear. It is also preferable that the largest cross-dimension of the outer flexible tube not exceed about 5.0 millimeters and be not smaller than about 1.0 millimeter. It should be noted, however, that many different cross-dimension sizes are acceptable for the catheter assembly and these will be apparent to those skilled in the art who are familiar with this invention.

It is highly preferable that the depth electrode within the secondary lumen be removable, thereby allowing continued fluid flow using the catheter after electrical sensing is no longer intended.

In other preferred embodiments, the catheter assembly includes an outer flexible tube having a proximal end, a fluid-flow lumen extending therealong to the proximal end, and at least one radial aperture through the wall communicating with the fluid-flow lumen, the tube further defining a channel adjacent to the tube wall and extending therealong to the proximal end, and a depth electrode within the channel, extending along the length thereof and out the proximal end, the depth electrode having spaced electrical contacts exposed along the flexible tube.

Preferably, the depth electrode is a medical-grade polyurethane material with a Shore A hardness of at least about 50. It is highly preferable that the polyurethane material for the depth electrode have a Shore A hardness of about 55. It is also preferable that the outer flexible tube be an integral piece of medical-grade elastomeric tube with Shore A hardness of at least about 80, most preferably about 83.

Another aspect of this invention is the method of using such catheter assembly. The method includes: providing a catheter assembly as described above; inserting the catheter assembly into the patient's brain, thereby facilitating concurrent electrical sensing and fluid flow; and withdrawing the depth electrode from the secondary lumen while the catheter assembly is within the patient's brain and thereby, allowing fluid flow to continue after electrical sensing is no longer intended.

The term "windows" as used herein means the openings in the outer tube extending to the secondary lumen such that the electrical contacts are exposed to brain tissue.

BRIEF DESCRIPTION OF THE DRAWINGS

The drawings illustrate a preferred embodiment including the above-noted characteristics and features of the device. The device will be readily understood from the descriptions and drawings. In the drawings.

DETAILED DESCRIPTION

Figure 1:
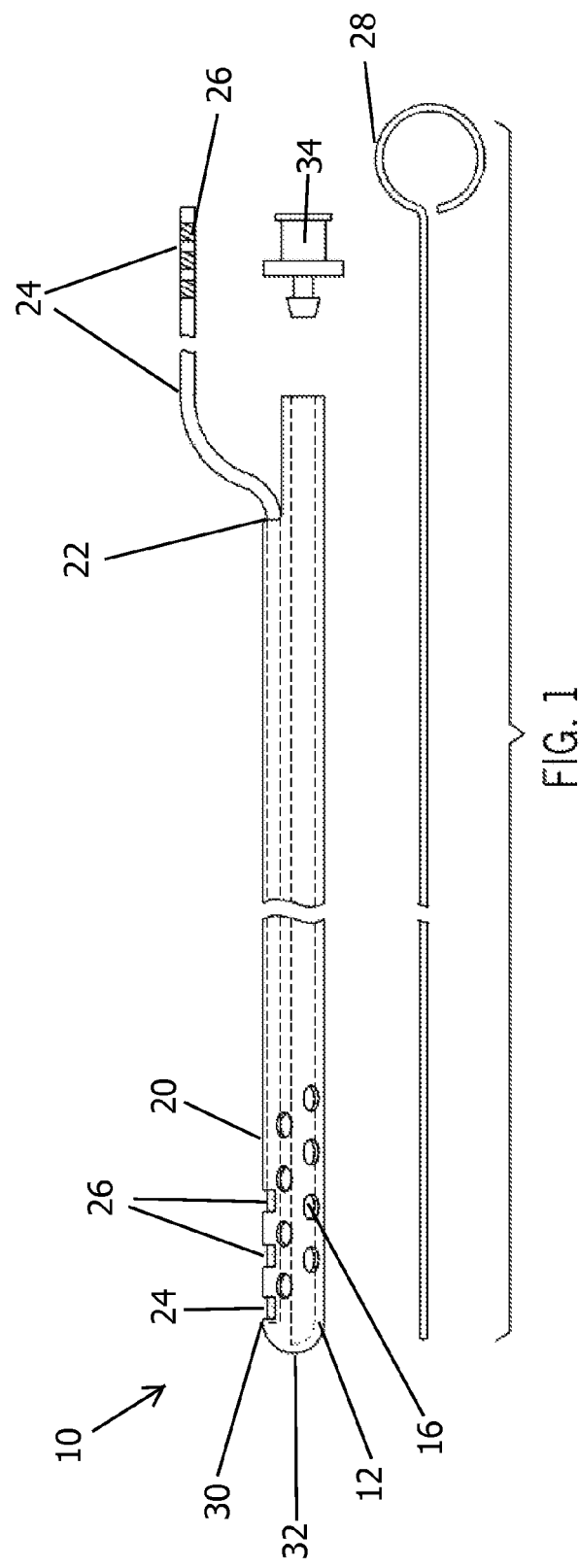
FIG. 1 is a side elevation of a catheter assembly in accordance with this invention, with its insertion stylet removed, and dotted lines indicating the internal locations of the principal and secondary lumens.

Referring to FIGS. 1-8, a catheter assembly in accordance with the present invention is generally designated by the reference numeral 10. Catheter assembly 10 allows intracranial treatment of a patient by providing an outer tube 12 and a principal lumen 14 as well as at least one radial aperture 16 through the wall communicating with the principal lumen 14 which cooperate to transfer fluids between a tissue region in the patient's brain and an external receptacle or device. Tube 12 further defines a secondary lumen 18 adjacent to the tube outer-wall surface 20 and extending therealong to a proximal end 22. Catheter assembly 10 includes a depth electrode 24 within secondary lumen 18 extending along the length thereof and out proximal end 22. Depth electrode 24 has spaced electrical contacts 26 exposed along tube 12 facilitating concurrent electrical sensing and fluid flow.

Figure 2:
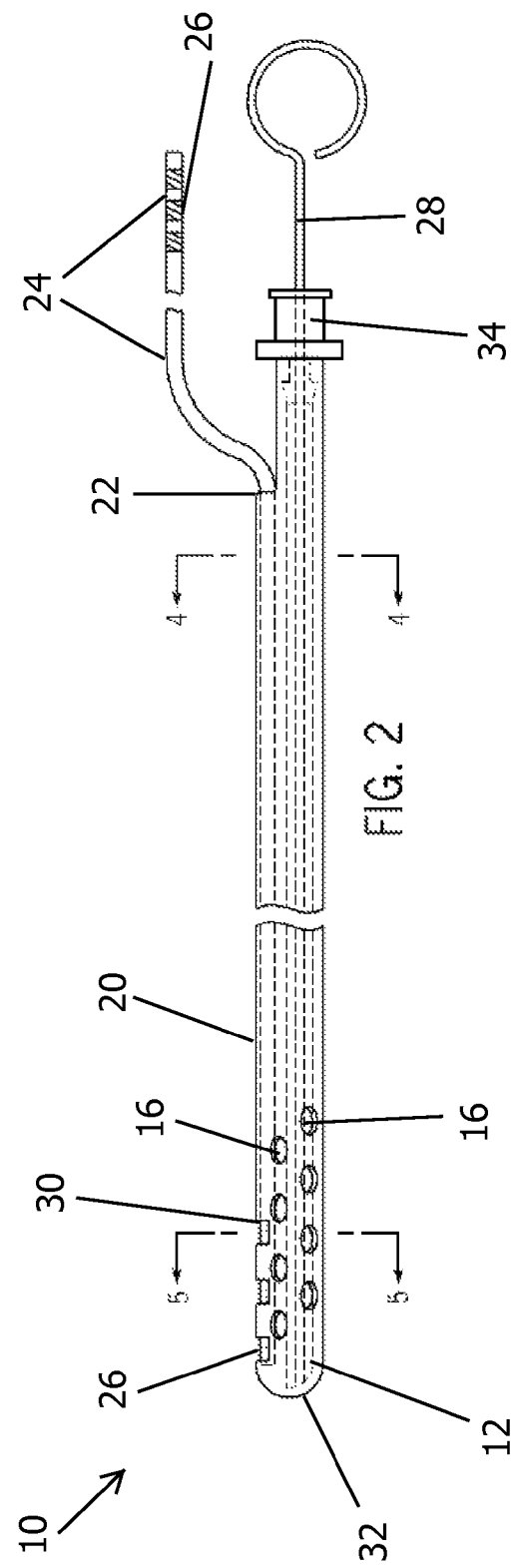
FIG. 2 is a similar side elevation of FIG. 1, but with the insertion stylet in place.
Figure 3:
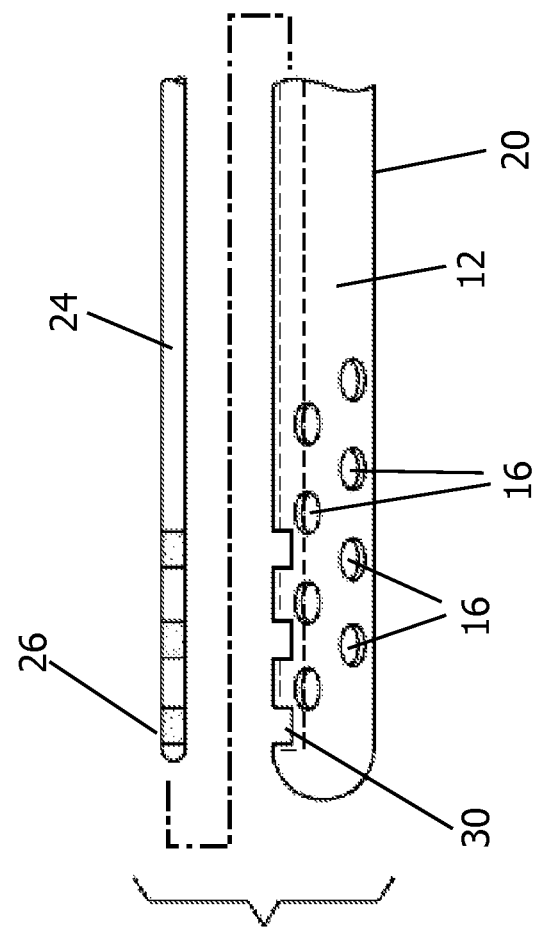
FIG. 3 is an enlarged, fragmentary, exploded view of the tip portion of the catheter assembly of FIG. 1.
Figure 7:
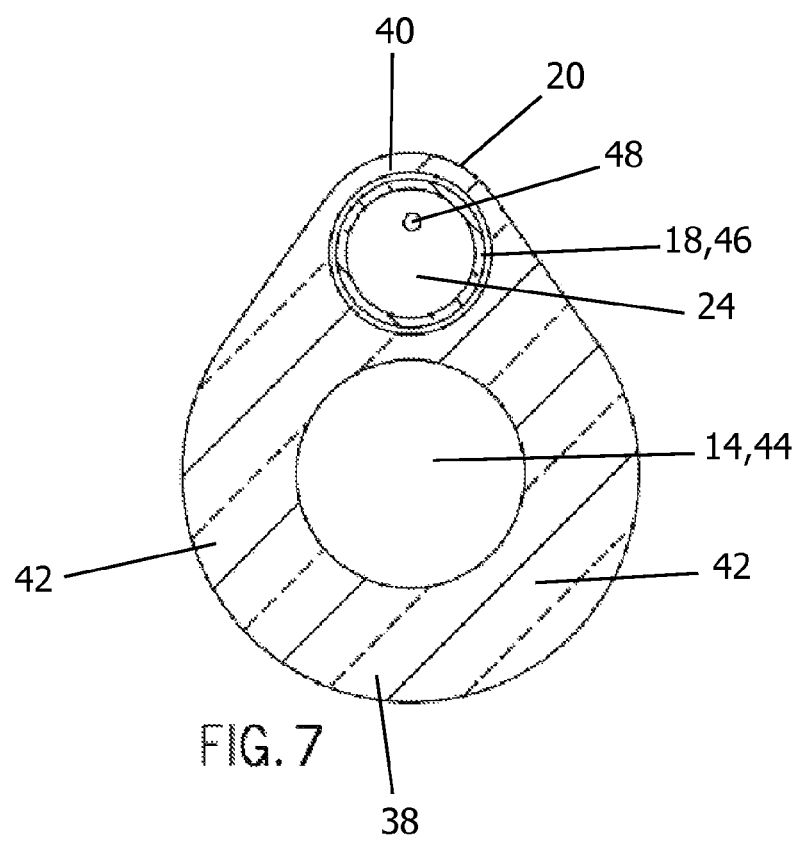
FIG. 7 is another cross-sectional view as in FIG. 4 but with the stylet having been removed.
Figure 8:
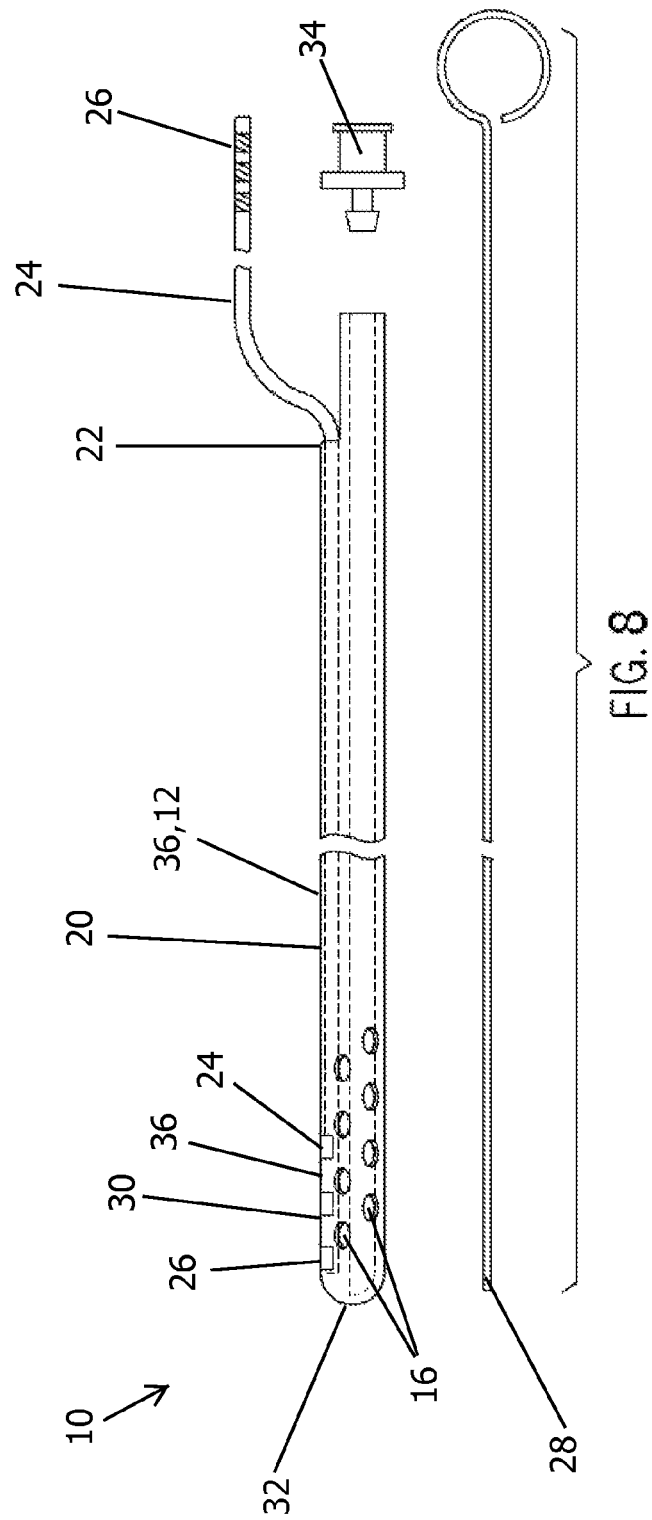
FIG. 8 is a side elevation of another catheter assembly similar to that of FIG. 1 except that the electrical contacts of the depth electrode have outer surfaces which are substantially flush with the outer surface of the outer-tube wall.
Figure 4:
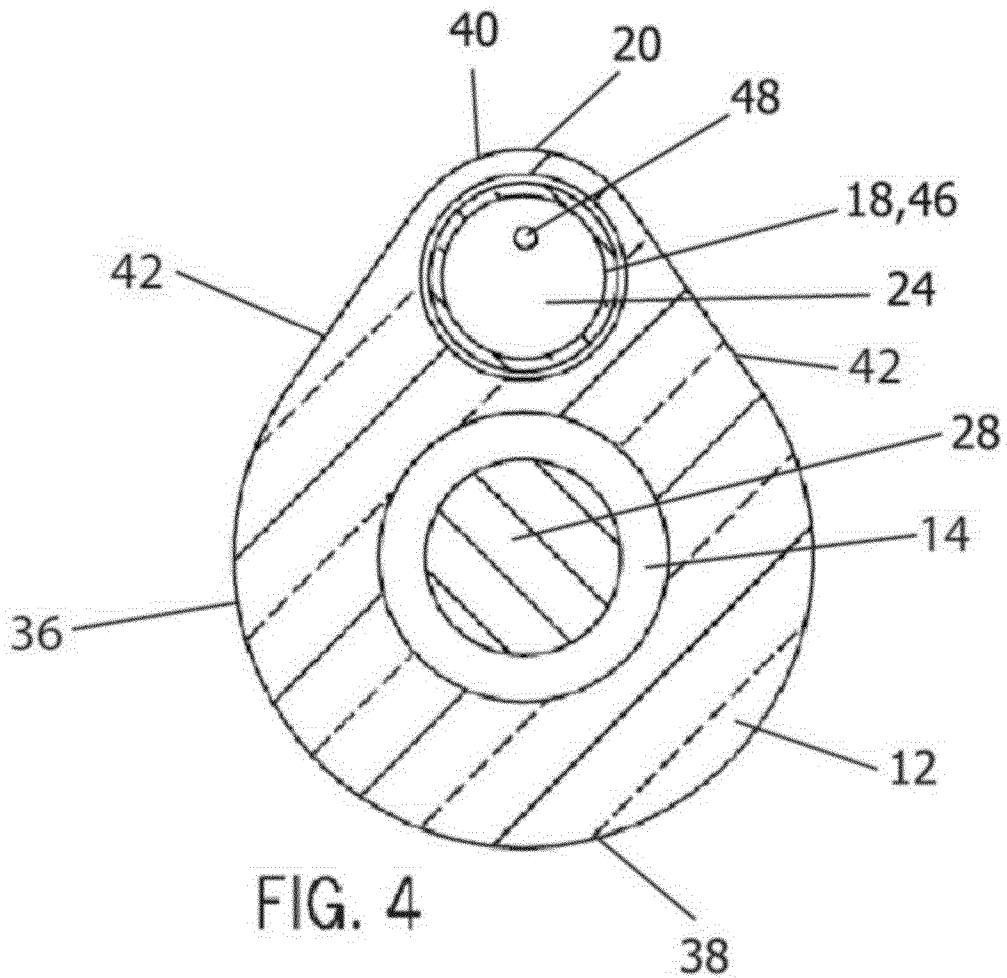

As seen in FIGS. 1-3, catheter assembly 10 includes windows 30 on tube 12 which extend through outer tube 12 and are aligned with electrical contacts 26 of depth electrode 24. In some embodiments, electrical contacts 26 along depth electrode 24 have diameters such that they extend at least partially into windows 30, thereby facilitating their electrical contact with brain tissue as seen in FIGS. 1-2. In another embodiment, electrical contacts 26 along depth electrode 24 are substantially flush with the outer-wall surface 36 of tube 12 as seen in FIG. 7. FIGS. 1-3 also illustrate that tube 12 includes a plurality of radial apertures 16 along and around tube 12.

FIG. 2 shows stylet 28 received within principal lumen 14 for insertion into the patient's brain. Stylet 28 provides rigidity to tube 12 if tube 12 is not rigid. Stylet 28 is generally removed after insertion of catheter assembly 10.

Tube 12 includes principal lumen 14 which extends from proximal end 22 to aperture 16 as seen in FIGS. 1-2. Principal lumen 14 has an inner diameter which may vary depending on the desired flow rate of fluid but is preferably between about 25 microns and 2.8 millimeters (drug delivery and drainage). It is very preferable that the inner diameter for principal lumen 14 is about 0.50 inches (1.3 millimeters). Depending on the size of principal lumen other insertion methods like a cannula may be used. Fluids may be transferred to or from a tissue region through principal lumen 14, e.g., drugs may be administered to tissue region, cerebral spinal fluid may be withdrawn, or both. FIG. 3 illustrates that depth electrode 24 within secondary lumen 18 is removable, thereby allowing for increased fluid flow after electrical sensing/monitoring is no longer intended.

FIG. 3 also illustrates that depth electrode 24 includes electrical contacts 26 which can provide monitoring of brain tissue or which can also provide a location marker for determining the precise position of tube 12 within the brain. Preferred contacts 26 are platinum, platinum iridium or other biocompatible conductive material. Brain activity sensed by contacts 26 is transmitted to an external connector and then to a computer or instrument which records and/or analyzes such activity. Contacts 26 are preferably stainless steel or other alloys or materials which are non-corrosive conductors which can endure the sterilization process.

As seen in FIGS. 1-2, depth electrode 24 includes two sets of electrical contacts 26, one set of electrical contacts 26 on proximal end 22 of depth electrode and one set of electrical contacts 26 on distal end 32 of depth electrode 24. (Proximal end 22 and distal end 32 of depth electrode 24 correlate with proximal end 22 and distal end 32 of outer tube 12.) Electrical contacts 26 are generally macro contacts of the collar-type which circumscribe outer surface of depth electrode 24. Contacts 26 on proximal end 22 of depth electrode 24 connect to contacts 26 on distal end 32 of depth electrode 24 to communicate (through wires 48) brain activity to a recording or analysis instrument. Contacts 26 on proximal end 22 do not enter the patient's brain, instead they provide connection to such an instrument.

Tube 12 has a closed distal end 32. A luer fitting 34, as shown in FIG. 1, is inserted into principal lumen 14 at proximal end 22 during treatment. Luer fitting 34 can function as a connector for connecting catheter assembly 10 with a drainage system or the like.

Cross-dimension of tube 12 is preferably between about 1.0 and 5.0 millimeters, most preferably about 2.5 millimeters and is comprised of polyurethane, silicone, polyimide, or other biocompatible material. Preferably, polyurethane material is used for tube 12. Polyurethane material is also preferably used for depth electrode 24.

It is desirable that the materials selected for tube 12 have a Shore A hardness of at least about 80 (on the Shore A scale of 0-100). A Shore A hardness of 83 is preferred for tube 12. It is also desirable that tube 12 be an integral piece of medical-grade elastomeric tube. (An "elastomer" is a polymeric compound with elastic properties.) It is desirably that depth electrode 24 is comprised of a polyurethane material having a Shore A hardness of at least about 50. A Shore A hardness of 55 is preferred for depth electrode 24. Persons of ordinary skill in the art will be aware of numerous other materials satisfying the requirements for tube 12 and depth electrode 24.

One skilled in the art will recognize that certain materials having resilient compressibility will have lower density than materials having lesser resilient compressibility. More often materials having greater resilient compressibility have a lower measure of hardness on the Shore A scale than less compressible materials. "Hardness" relates to compressibility of the material; the harder a material, the less compressible it is, and vice versa. Hardness also relates to resistance to deformation under pressure.

Figure 4:
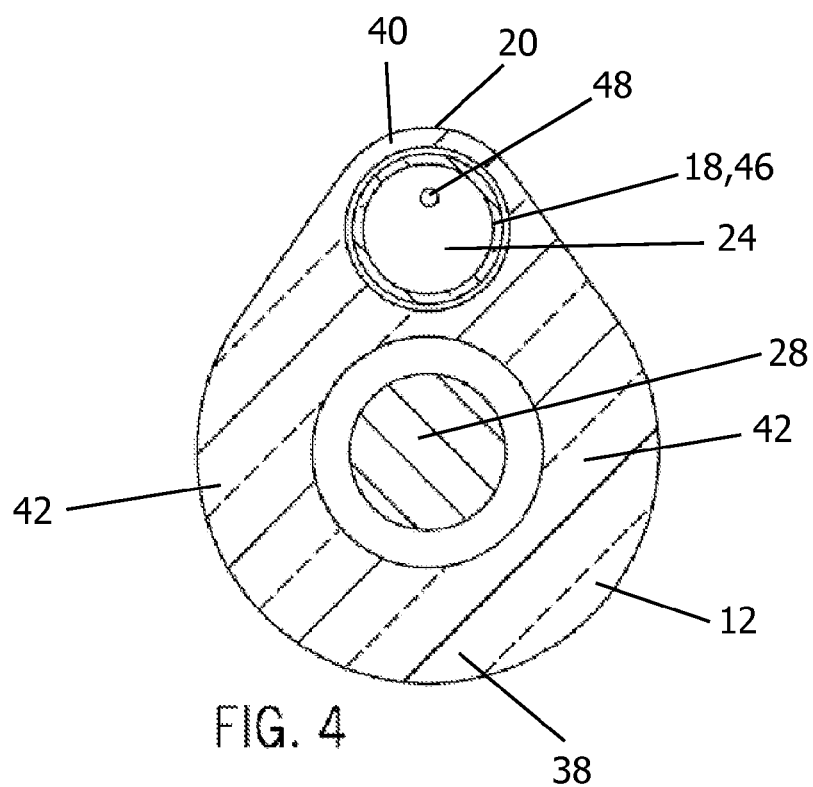
FIG. 4 is an enlarged cross-sectional view of the catheter assembly taken along section 4-4 as indicated in FIG. 2.
Figure 5:
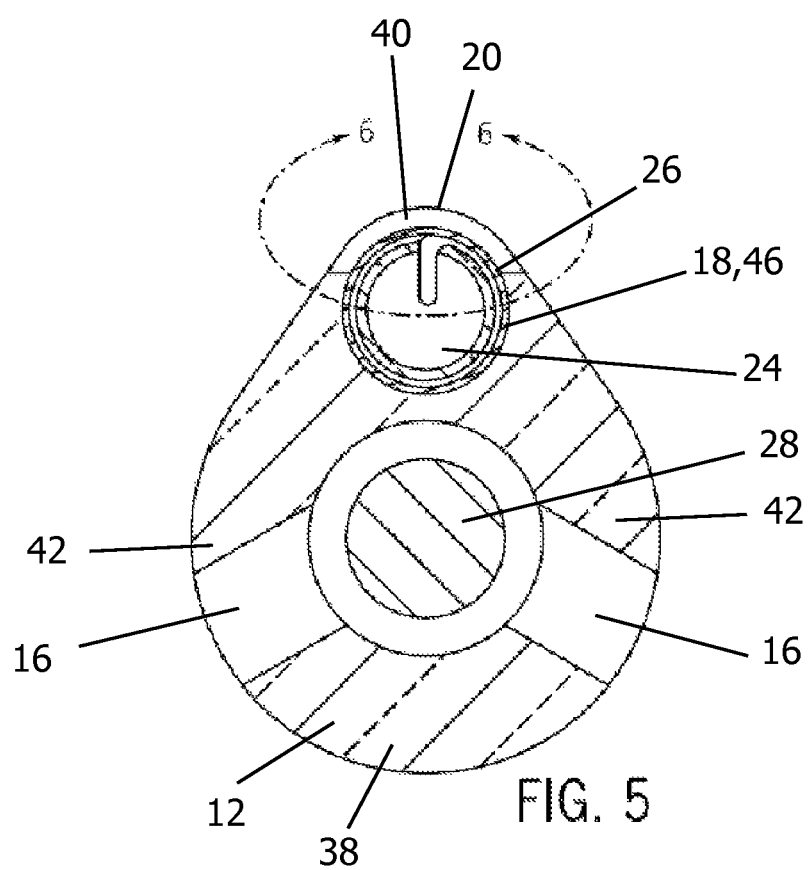
FIG. 5 is an enlarged cross-sectional view of the catheter assembly taken along section 5-5 as indicated in FIG. 2.
Figure 6:
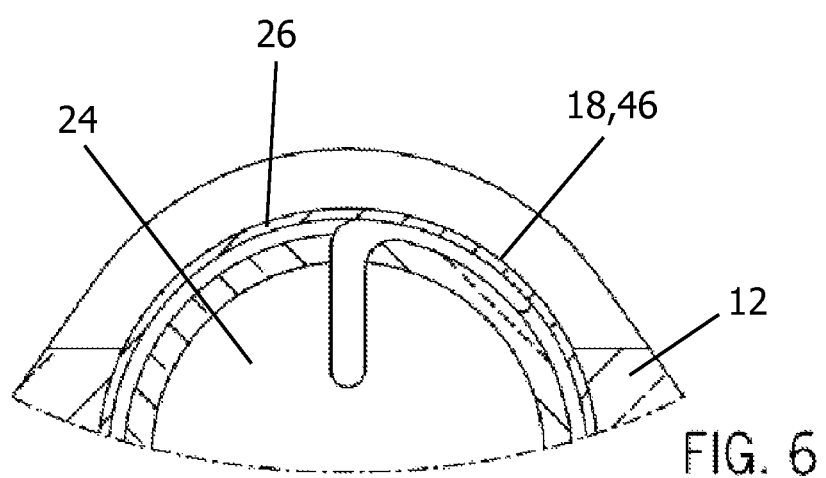
FIG. 6 is a further enlarged fragmentary view of FIG. 5 as indicated by portion 6-6.

FIGS. 4-6 illustrate that in cross-section, principal and secondary lumens 14, 18 are substantially circular, the size of secondary lumen 18 being smaller than the size of principal lumen 14. It is preferable that the inner diameter for secondary lumen 18 is about 0.034 inches. Tube outer-wall surface 36 is substantially smooth and has a major cylindrical portion 38 substantially parallel to the surface of principal lumen 14, a minor cylindrical portion 40 substantially parallel to the surface of secondary lumen 18, and transitional portions 42 therebetween on either side. In some embodiments transitional portions 42 (in cross-section) are other than concave. In other embodiments transitional portions 42 (in cross-section) are substantially linear.

While many dimensions are acceptable, it is preferably that the largest cross-dimension of tube 12 does not exceed about 5.0 millimeters and be not smaller than about 1.0 millimeter.

An alternate embodiment of catheter assembly 10 includes tube 12 having proximal end 22, a fluid-flow lumen 44 extending therealong to proximal end 22, and at least one radial aperture 16 through tube wall 36 communicating with lumen 44. Tube 12 further defines a channel 46 adjacent to tube wall 36 and extending therealong to proximal end 22. Depth electrode 24 can be removably withdrawn from channel 46, extending along the length thereof and out proximal end 22. Depth electrode 24 includes spaced electrical contacts 26 exposed along tube 12.

In a highly preferred method, a catheter assembly 10 is provided including (a) an outer flexible tube 12 having a proximal end 22, a principal lumen 14 extending therealong to the proximal end 22, and at least one radial aperture 16 through the wall communicating with the lumen 14, tube 12 further defining a secondary lumen 18 adjacent to the tube outer-wall 20 surface and extending therealong to proximal end 22, and (b) a depth electrode 24 within secondary lumen 18, extending along the length thereof and out proximal end 22, depth electrode 24 having spaced electrical contacts 26 exposed along tube 12; (2) inserting the catheter assembly 10 into the patient's brain, thereby facilitating concurrent electrical sensing and fluid flow; and (3) withdrawing depth electrode 24 from secondary lumen 18 while catheter assembly 10 is within the patient's brain thereby, allowing fluid flow after electrical sensing is no longer intended.

A wide variety of materials are available for the various parts discussed and illustrated herein. While the principles of this invention have been described in connection with specific embodiments, it should be understood clearly that these descriptions are made only by way of example and are not intended to limit the scope of the invention.

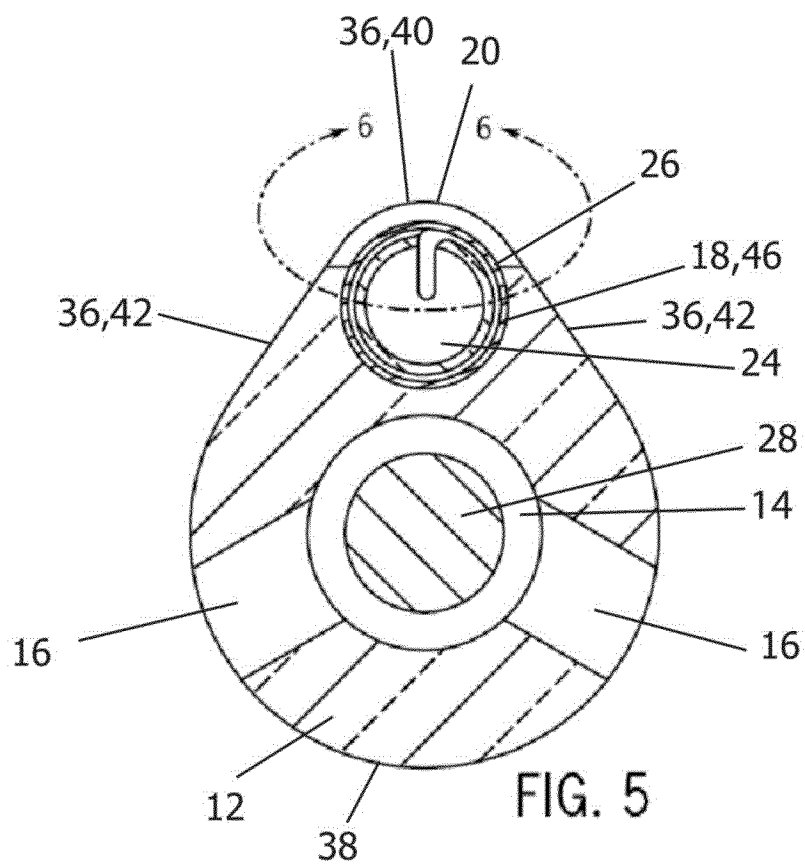

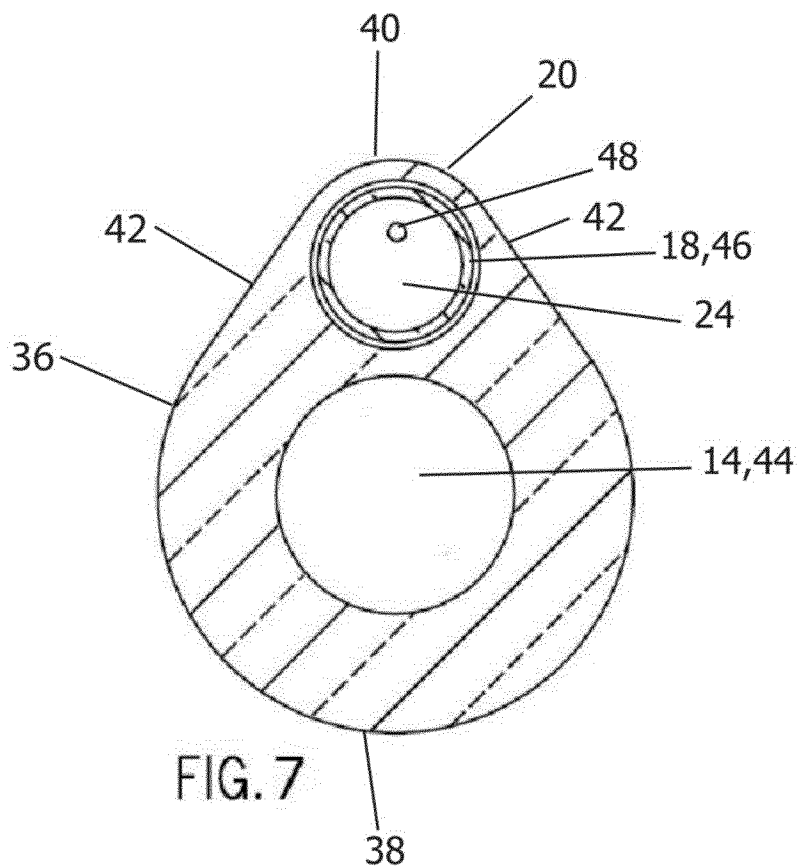

The invention claimed is:

1. A catheter assembly for intracranial treatment of a patient comprising:
an outer flexible tube having a proximal end, a principal lumen extending therealong to the proximal end, and at least one radial aperture through the wall communicating with the lumen, the tube further defining a secondary lumen adjacent to the tube outer-wall surface and extending therealong to the proximal end, in cross-section the principal and secondary lumens are substantially circular, the size of the secondary lumen being smaller than the size of the principal lumen and the tube outer-wall surface is substantially smooth and has a major cylindrical portion substantially parallel to the surface of the principal lumen, a minor cylindrical portion substantially parallel to the surface of the secondary lumen, and transitional portions therebetween on either side, each transitional portion being other than concave; and
a depth electrode within the secondary lumen, extending along the length thereof and out the proximal end, the depth electrode having spaced electrical contacts exposed along the flexible tube,
thereby facilitating concurrent electrical sensing and fluid flow.

2. The catheter assembly of claim 1 wherein the outer tube includes windows therethrough aligned with the electrical contacts of the depth electrode.

3. The catheter assembly of claim 1 wherein there are a plurality of radial apertures along and around the outer tube.

4. The catheter assembly of claim 3 wherein the outer tube includes windows therethrough aligned with the electrical contacts of the depth electrode.

5. The catheter assembly of claim 1 wherein the outer tube has a closed distal end.

6. The catheter assembly of claim 5 further comprising a rigid stylet received within the principal lumen during and for purposes of insertion into the patient's brain, the stylet being removable after insertion of the catheter assembly.

7. The catheter assembly of claim 6 wherein the outer tube includes windows therethrough aligned with the electrical contacts of the depth electrode.

8. The catheter assembly of claim 6 wherein there are a plurality of radial apertures along and around the outer tube.

9. The catheter assembly of claim 8 wherein the outer tube includes windows therethrough aligned with the electrical contacts of the depth electrode.

10. The catheter assembly of claim 1 further including a luer fitting inserted into the principal lumen at the proximal end during treatment, the luer fitting being a connector for connecting the catheter assembly with a drainage system.

11. The catheter assembly of claim 10 wherein the outer tube includes windows therethrough aligned with the electrical contacts of the depth electrode.

12. The catheter assembly of claim 10 wherein there are a plurality of radial apertures along and around the outer tube.

13. The catheter assembly of claim 12 wherein the outer tube includes windows therethrough aligned with the electrical contacts of the depth electrode.

14. The catheter assembly of claim 2 wherein the electrical contacts along the depth electrode have diameters such that they extend at least partially into the windows, thereby facilitating their electrical contact with brain tissue.

15. The catheter assembly of claim 14 wherein the electrical contacts along the depth electrode are substantially flush with the outer-wall surface.

16. The catheter assembly of claim 1 wherein in cross-section each transitional portion is substantially linear.

17. The catheter assembly of claim 1 wherein the largest cross-dimension of the outer flexible tube does not exceed about 5.0 millimeters and the smallest cross-dimension is not smaller than about 1.0 millimeter.

18. The catheter assembly of claim 1 wherein the depth electrode within the secondary lumen is removable, thereby allowing fluid flow after electrical sensing is no longer intended.

19. A catheter assembly for intracranial treatment of a patient comprising:
an outer flexible tube having a proximal end, a fluid-flow lumen extending therealong to the proximal end, and at least one radial aperture through the wall communicating with the lumen, the tube further defining a channel adjacent to the tube wall and extending therealong to the proximal end, in cross-section the fluid-flow lumen and channel are substantially circular, the size of the channel being smaller than the size of the fluid-flow lumen and the tube outer-wall surface is substantially smooth and has a major cylindrical portion substantially parallel to the surface of the fluid-flow lumen, a minor cylindrical portion substantially parallel to the surface of the channel, and transitional portions therebetween on either side, each transitional portion being other than concave; and a depth electrode within the channel, extending along the length thereof and out the proximal end, the depth electrode having spaced electrical contacts exposed along the flexible tube.

20. The catheter assembly of claim 19 wherein the outer tube includes windows therethrough aligned with the electrical contacts of the depth electrode.

21. The catheter assembly of claim 19 wherein there are a plurality of radial apertures along and around the outer tube.

22. The catheter assembly of claim 1 wherein the depth electrode includes a tube of a polyurethane material having a Shore A hardness of at least about 50.

23. The catheter assembly of claim 22 wherein the polyurethane material has a Shore A hardness of 55.

24. The catheter assembly of claim 1 wherein the outer flexible tube is an integral piece of medical-grade elastomeric tube having a Shore A hardness of at least about 80.

25. The catheter assembly of claim 24 wherein the polyurethane material has a Shore A hardness of 83.

26. The catheter assembly of claim 24 wherein the depth electrode includes a tube of a polyurethane material having a Shore A hardness of at least about 50.

27. A method for intracranial treatment of a patient comprising:

providing a catheter assembly including (a) an outer flexible tube having a proximal end, a principal lumen extending therealong to the proximal end, and at least one radial aperture through the wall communicating with the lumen, the tube further defining a secondary lumen adjacent to the tube outer-wall surface and extending therealong to the proximal end, in cross-section the principal and secondary lumens are substantially circular, the size of the secondary lumen being smaller than the size of the principal lumen and the tube outer-wall surface is substantially smooth and has a major cylindrical portion substantially parallel to the surface of the principal lumen, a minor cylindrical portion substantially parallel to the surface of the secondary lumen, and transitional portions therebetween on either side, each transitional portion being other than concave, and (b) a depth electrode within the secondary lumen, extending along the length thereof and out the proximal end, the depth electrode having spaced electrical contacts exposed along the flexible tube;

inserting the catheter assembly into the patient's brain, thereby facilitating concurrent electrical sensing and fluid flow; and withdrawing the depth electrode from the secondary lumen while the catheter assembly is within the patient's brain thereby, allowing fluid flow after electrical sensing is no longer intended.

\* \* \* \* \*

UNITED STATES PATENT AND TRADEMARK OFFICE
CERTIFICATE OF CORRECTION

PATENT NO. : 9,072,864 B2  
APPLICATION NO. : 13/687254  
DATED : July 7, 2015  
INVENTOR(S) : David A. Putz It is certified that error appears in the above-identified patent and that said Letters Patent is hereby corrected as shown below:

In the Drawings

Please replace Figs. 4, 5, and 7 with Figs. 4, 5, and 7 as shown on the attached pages.

Signed and Sealed this
Fourteenth Day of April, 2020

Andrei Iancu
*Director of the United States Patent and Trademark Office*